US005449003A

United States Patent [19]

Sugimura

[11] Patent Number: 5,449,003

[45] Date of Patent: Sep. 12, 1995

[54] UNDULATED CONTAINER FOR UNDULATED DIAPHRAGM AND DIAPHRAGM DEVICE

[76] Inventor: Kazuo Sugimura, 3-27, Mabasekita, Shimizu-shi, Shizuoka, Japan, 424

[21] Appl. No.: 172,584

[22] Filed: Dec. 23, 1993

[30] Foreign Application Priority Data

Dec. 28, 1992 [JP] Japan ............ 4-092977 U
Dec. 28, 1992 [JP] Japan ............ 4-358689

[51] Int. Cl.$^{6}$ ............ A61F 6/06; F01B 19/00

[52] U.S. Cl. ............ 128/830; 92/89

[58] Field of Search ............ 128/830–841; 92/96, 97, 98, 100, 104, 89

[56] References Cited

U.S. PATENT DOCUMENTS

| | | | |
|---|---|---|---|
| 3,385,477 | 5/1968 | Chevalaz | 92/104 |
| 3,523,857 | 8/1970 | Crosland | 92/96 |
| 3,545,070 | 12/1970 | Bauer | 92/100 |
| 3,722,373 | 3/1973 | Beach | 92/104 |
| 4,028,566 | 6/1977 | Franssen | 29/25.35 |
| 4,375,182 | 3/1983 | Zavoda | 92/104 |
| 4,666,378 | 5/1987 | Ogawa | 92/100 |
| 5,064,165 | 11/1991 | Jerman | 92/104 |
| 5,215,124 | 6/1993 | Hattori et al. | |
| 5,335,584 | 8/1994 | Baird | 92/96 |

FOREIGN PATENT DOCUMENTS

| | | |
|---|---|---|
| 8423974 | 12/1984 | Germany . |
| 4-101801 | 9/1992 | Japan . |
| 540036 | 10/1941 | United Kingdom . |
| 571616 | 8/1945 | United Kingdom . |
| 575456 | 2/1946 | United Kingdom . |
| 702518 | 1/1954 | United Kingdom . |

*Primary Examiner*—Michael A. Brown
*Attorney, Agent, or Firm*—Brumbaugh, Graves, Donohue & Raymond

[57] ABSTRACT

An undulated diaphragm, which has an approximately circular, flat plate-shaped central portion and a peripheral portion composed of a series of alternate, approximately concentric convex and concave portions, is clamped between two undulated container members each having an approximately bowl-shaped recess. The recesses of the container members are each composed of a series of alternate, approximately concentric concave and convex portions, which are complementally formed to correspond to the approximately concentric convex and concave portions of the diaphragm when extended. When the pressure in one recess is raised, the diaphragm successively moves toward the other recess and finally comes in contact with the second recess completely and snugly fits thereto. When the pressure in the first recess is lowered, the diaphragm successively moves toward the first recess and finally comes in contact with the first recess completely and snugly fits thereto. Deformation of the diaphragm during movement is restricted by virtue of the elasticity and rigidity of the diaphragm and the structure thereof, which includes a series of alternate, approximately concentric convex and concave portions. Thus, the diaphragm regularly extends and contracts without causing local inversion of the direction of bending during the movement.

10 Claims, 8 Drawing Sheets

UNDULATED CONTAINER FOR UNDULATED DIAPHRAGM AND DIAPHRAGM DEVICE

BACKGROUND OF THE INVENTION

The present invention relates to an undulated container for an undulated diaphragm and a diaphragm device, which may be used in a diaphragm accumulator, diaphragm pump, diaphragm actuator and so forth of the type in which a diaphragm is clamped between two container members each having an approximately bowl-shaped recess.

A diaphragm accumulator of the type in which a diaphragm is clamped between two container members each having an approximately bowl-shaped recess, as shown in the sectional view of FIG. 14, has heretofore been known. In the conventional diaphragm accumulator, a pan-shaped diaphragm 51 has a literally pan-shaped configuration as a whole. The central portion 2 of the pan-shaped diaphragm 51 has an approximately circular flat plate-shaped configuration. The outer periphery of the moving portion of the pan-shaped diaphragm 51 has an approximately frusto-conical configuration. The diaphragm accumulator includes a main body (first container member) 6 and a side plate (second container member) 7. The mutually opposing surfaces of the body 6 and the side plate 7 have approximately pan-shaped recesses 49 (on the body 6) and 50 (on the side plate 7) formed in the respective central portions. The body 6 has a stepped annular clamp portion 15 formed outwardly of the recess 49. Similarly, the side plate 7 has a stepped annular clamp portion 16 formed outwardly of the recess 50. The clamp portion 15 is formed with a first annular groove 17. The clamp portion 16 has a second annular groove 18 formed at a position which faces the first annular groove 17. The first and second annular grooves 17 and 18 are fitted with first and second seal members 11 and 12, respectively. The outer peripheral portion of the pan-shaped diaphragm 51 is clamped between the clamp portions 15 and 16. A plurality of bolts 22 are inserted into respective pairs of bolt holes 19 and 20, which are formed in the body 6 and the side plate 7, and nuts 23 are screwed onto the bolts 22, respectively. In this way, the outer peripheral portion of the pan-shaped diaphragm 51 is clamped between the clamp portions 15 and 16, and the area between the recesses 49 and 50 on the upper and lower sides of the pan-shaped diaphragm 51 is hermetically sealed by the first and second seal members 11 and 12. The space between the recess 50 of the side plate 7 and the pan-shaped diaphragm 51 is defined as a gas chamber (second chamber) 13, which is sealingly charged with a gas through a connecting opening 28 formed in the side plate 7. Similarly, the space between the recess 49 of the body 6 and the pan-shaped diaphragm 51 is defined as a fluid chamber (first chamber) 14, into which an external fluid is introduced through a supply and discharge opening 25 and a connecting opening 26, which are formed in the body 6.

In response to a change of the pressure in the fluid chamber 14, the pan-shaped diaphragm 51 is deflected to move toward the gas chamber 13 or the fluid chamber 14, and at an extremity of the deflection thereof, the pan-shaped diaphragm 51 comes in contact with either the recess 49 or 50. The position of the pan-shaped diaphragm 51 changes as shown by the alternate long and short dash lines in FIG. 14. That is, the pan-shaped diaphragm 51 can move from a position E where it completely comes in contact with the recess 49 to a position A where it completely comes in contact with the recess 50, via positions D, C and B. When the pan-shaped diaphragm 51 moves from the position E to the position A and also from the position E to the position B, most portions of the pan-shaped diaphragm 51 are irregularly deformed without coming in contact with the body 6. An example of the irregular deformation is local inversion of the direction of bending which occurs on the pan-shaped diaphragm 51 during movement. Local inversion of the bending direction is such a phenomenon that when the pan-shaped diaphragm 51 is moving toward the gas chamber 13 or the fluid chamber 14 in its entirety, the diaphragm 51 locally changes its shape from convex to concave or the reverse. On the other hand, when the pan-shaped diaphragm 51 moves from the position A to the position B and vice versa, the peripheral edge of the moving portion of the diaphragm 51 changes the bending direction from bending toward the recess 49 to bending toward the recess 50 or the reverse at the peripheral edge 5 of the gas and fluid chambers 13 and 14. Thus, irregular deformation such as local inversion of the bending direction of the pan-shaped diaphragm 51 occurs at many portions of the pan-shaped diaphragm 51, and a change of a curve from bending toward the recess 49 to bending toward the recess 50 or the reverse occurs at the peripheral edge of the moving portion of the pan-shaped diaphragm 51. Repetition of such deformation, particularly bending, causes the inflective portions to become fatigue. Consequently, the inflective portions rapidly deteriorate in strength and become easy to break.

A technique whereby the above-described disadvantage is partially overcome is disclosed in Japanese Utility Model Application Kokai No. 4-101801, which was laid open to public inspection in Japan on Sep. 2, 1992, although the disclosed technique is intended for a diaphragm accumulator of the type in which a diaphragm is attached to a spherical shell so as to face toward the fluid chamber.

In the diaphragm accumulator, the outer peripheral surface of the peripheral edge of a diaphragm (bladder) is brought into contact with the inner peripheral surface of a spherical body (shell), and an elastic mounting portion formed on the inner peripheral surface of the peripheral edge of the diaphragm is secured by a mounting member, thereby dividing the interior space of the body into a gas chamber and a liquid chamber by the diaphragm. In addition, an inward projection is formed on the inner peripheral surface of the body at the same distance from the elastic mounting portion, thereby reducing the distance between the inner peripheral surface of the body and at least the inner point of inflection of the inner and outer points of inflection of the inflective portion of an elastic material layer constituting the diaphragm, and thus increasing the buckling stress of the elastic material layer at at least the inner point of inflection of the inflective portion of the diaphragm. In doing so, the buckling stress is allowed to approach the rupture stress, thereby suppressing buckling of the elastic material layer.

In the diaphragm accumulator disclosed in the above publication, as the pressure in the liquid chamber lowers, the diaphragm moves toward and also along the above-described projection in the liquid chamber. In this case, the diaphragm is regularly deformed while being in contact with the inner surface of the body.

However, after the diaphragm has passed the projection, irregular deformation occurs. When the diaphragm moves toward the gas chamber in response to an increase of the pressure in the liquid chamber, the diaphragm is irregularly deformed without coming in contact with the body. Irregular deformation includes, for example, local inversion of the bending direction of the diaphragm during movement as described above. Accordingly, the diaphragm locally changes its shape from convex to concave or the reverse. Repetition of local inversion of the bending direction causes the inflective portions to become fatigue. Consequently, the inflective portions rapidly deteriorate in strength and become easy to break.

OBJECTS AND SUMMARY OF THE INVENTION

A first object of the present invention is to provide a diaphragm container of the type in which a diaphragm is clamped between two container members each having an approximately bowl-shaped recess, which is designed so that deformation of the diaphragm during movement is restricted so as to be regular, thereby minimizing fatigue of the diaphragm caused by local inversion of the bending direction of the diaphragm during movement thereof, and thus improving the durability of the diaphragm and increasing the lifetime thereof.

A second object of the present invention is to provide a diaphragm device of the type in which a diaphragm is clamped between two container members each having an approximately bowl-shaped recess, which is designed so that when the diaphragm moves from the recess of the first container member toward the recess of the second container member or the reverse, inversion of the bending direction of the diaphragm is prevented from repeatedly occurring at the same portion of the diaphragm at the peripheral edges of the recesses, thereby minimizing fatigue of the diaphragm, and thus improving the durability of the diaphragm and increasing the lifetime thereof.

A third object of the present invention is to provide a diaphragm device of the type in which a diaphragm is clamped between two container members each having an approximately bowl-shaped recess, which is designed so that when the diaphragm moves from the recess of the first container member toward the recess of the second container member or the reverse, inversion of the bending direction of the diaphragm is prevented from repeatedly occurring at the same portion of the diaphragm at the peripheral edges of the recesses, and at the same time, deformation of the diaphragm during movement is restricted so as to be regular, thereby eliminating local inversion of the bending direction of the diaphragm during movement thereof, and thus improving the durability of the diaphragm and increasing the lifetime thereof.

The present invention provides an undulated diaphragm container in which an undulated diaphragm, which has an approximately circular, flat plate-shaped central portion and a peripheral portion composed of a series of alternate, approximately concentric convex and concave portions, is clamped between two container members each having an approximately bowl-shaped recess. At least one of the recesses of the container members has a wall surface undulated so as to match the diaphragm when extended. In the present invention, when the diaphragm is moving toward either of the recesses in its entirety, no local inversion occurs at any of the convex and concave portions, which are approximately concentric with respect to each other. Therefore, the convex portions always maintain their convex shape. Similarly, the concave portions always maintain their concave shape. When the diaphragm is extended toward the recess having the undulated wall surface, the convex and concave portions of the diaphragm snugly fit to the concave and convex portions, respectively, of the container member facing the diaphragm.

In addition, the present invention provides a diaphragm device in which a diaphragm is clamped between a pair of first and second container members each having an approximately bowl-shaped recess so that a first chamber is defined between the recess of the first container member and the diaphragm, and a second chamber is defined between the recess of the second container member and the diaphragm. The recesses of the first and second container members have different diameters so that a first position where the diaphragm begins to bend toward the recess of the first container member at the peripheral edge of this recess and a second position where the diaphragm begins to bend toward the recess of the second container member at the peripheral edge of this recess are different from each other.

DETAILED DESCRIPTION OF THE EMBODIMENTS

Figure 1:
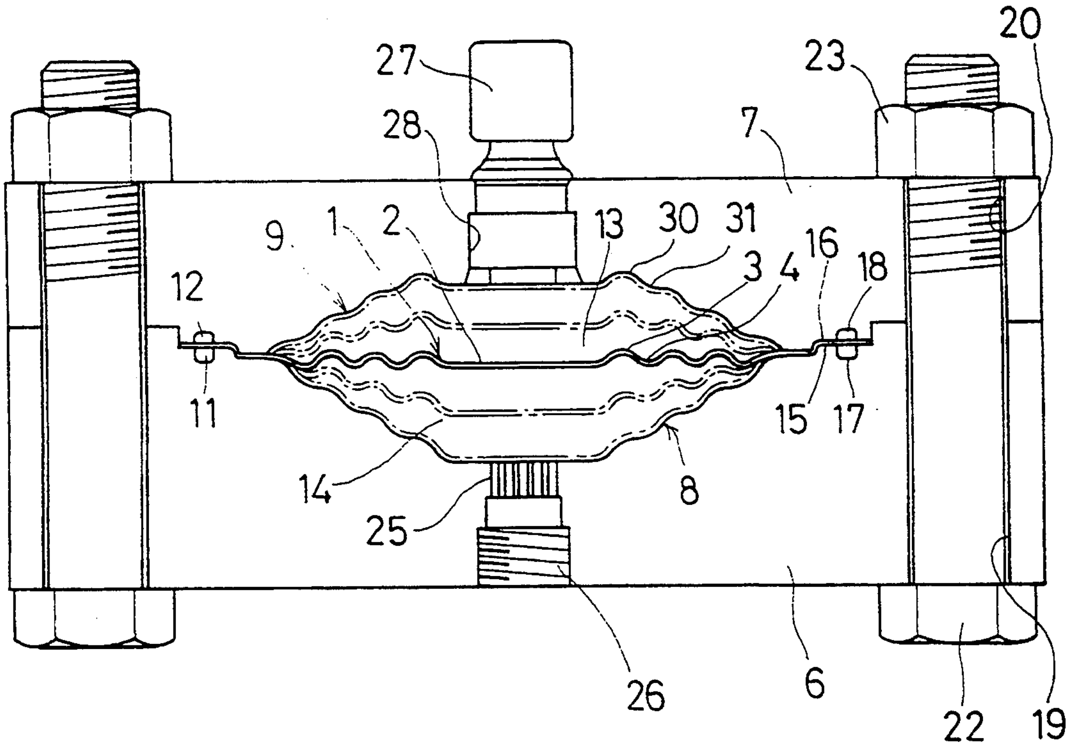
FIG. 1 is a sectional view of an undulated diaphragm container according to a first embodiment of the present invention.

An undulated diaphragm container according a first embodiment of the present invention will be described below with reference to FIGS. 1 and 2. FIG. 1 is a sectional view of an undulated diaphragm container of the present invention which is applied to a diaphragm accumulator. An undulated diaphragm 1 includes a moving portion which has an approximately circular plate-shaped configuration. The undulated diaphragm 1 has an approximately circular, flat plate-shaped central portion, and a series of alternate, approximately concentric (annular) convex and concave portions 3 and 4, which are formed in a circular wave pattern at the outer periphery of the central portion 2. The contour of the convex and concave portions 3 and 4 is a curved line based on a sinusoidal wave, but it may be variously changed by experiment. The material of the diaphragm may be a metallic plate. In this embodiment, however, polytetrafluoroethylene (trade name: Teflon), which is superior in chemical resistance, is used. More specifically, a polytetrafluoroethylene plate of 0.3 mm or 0.5 mm in thickness is employed after being properly processed. The diaphragm accumulator includes a body (first container member) 6 and a side plate (second container member) 7. The mutually opposing surfaces of the body 6 and the side plate 7 have undulated recesses 8 (on the body 6) and 9 (on the side plate 7) formed in the respective central portions. The body 6 has a stepped annular clamp portion 15 formed outwardly of the recess 8. Similarly, the side plate 7 has a stepped annular clamp portion 16 formed outwardly of the recess 9. The clamp portion 15 is formed with a first annular groove 17. The clamp portion 16 has a second annular groove 18 formed at a position which faces the first annular groove 17. The first and second annular grooves 17 and 18 are fitted with first and second seal members 11 and 12, respectively. The outer peripheral portion of the diaphragm 1 is clamped between the clamp portions 15 and 16. A plurality of bolts 22 are inserted into respective pairs of bolt holes 19 and 20, which are formed in the body 6 and the side plate 7, and nuts 23 are screwed onto the bolts 22, respectively. In this way, the outer peripheral portion of the diaphragm 1 is clamped between the clamp portions 15 and 16, and the area between the recesses 8 and 9 on the upper and lower sides of the diaphragm 1 is hermetically sealed by the first and second seal members 11 and 12. The space between the recess 9 of the side plate 7 and the diaphragm 1 is defined as a gas chamber (second chamber) 13, which is sealingly charged with a gas through a gas supply opening 27 connected to a connecting opening 28 formed in the side plate 7. Similarly, the space between the recess 8 of the body 6 and the diaphragm 1 is defined as a fluid chamber (first chamber) 14, into which an external fluid is introduced through a supply and discharge opening 25 and a connecting opening 26, which are formed in the body 6. The diaphragm accumulator is used to absorb pulsation, surge pressure, etc. of a fluid. For example, it is used when a coating solution is sprayed to absorb pulsation of the coating fluid to thereby hold the fluid pressure constant.

In response to a change of the pressure in the fluid chamber 14, the undulated diaphragm 1 is deflected to move toward the gas chamber 13 or the fluid chamber 14. As a result of this movement, the diaphragm 1 comes in contact with the recess 8 or 9. Portions of the wall surfaces of the recesses 8 and 9 which are contacted by the diaphragm 1 are each composed of a series of alternate, approximately concentric concave and convex portions 30 and 31, which are complementally formed to correspond to the approximately concentric convex and concave portions 3 and 4 of the diaphragm 1 when extended. That is, when the diaphragm 1 is extended toward the gas chamber 13, for example, to come in contact with the wall surface of the recess 9 completely, the convex and concave portions 3 and 4 of the diaphragm 1 come in contact with the concave and convex portions 30 and 31, respectively, which are formed on the recess 9, and snugly fit thereto. In FIG. 1, the diaphragm 1 which is in a state where the internal volume of the gas chamber 13 and that of the fluid chamber 14 are equal to each other is shown by the solid lines. At this time, the diaphragm 1 lies at a position intermediate between the gas and fluid chambers 13 and 14, that is, in an approximately horizontal, central position where the whole diaphragm 1 does not lean toward either side.

Figure 2:
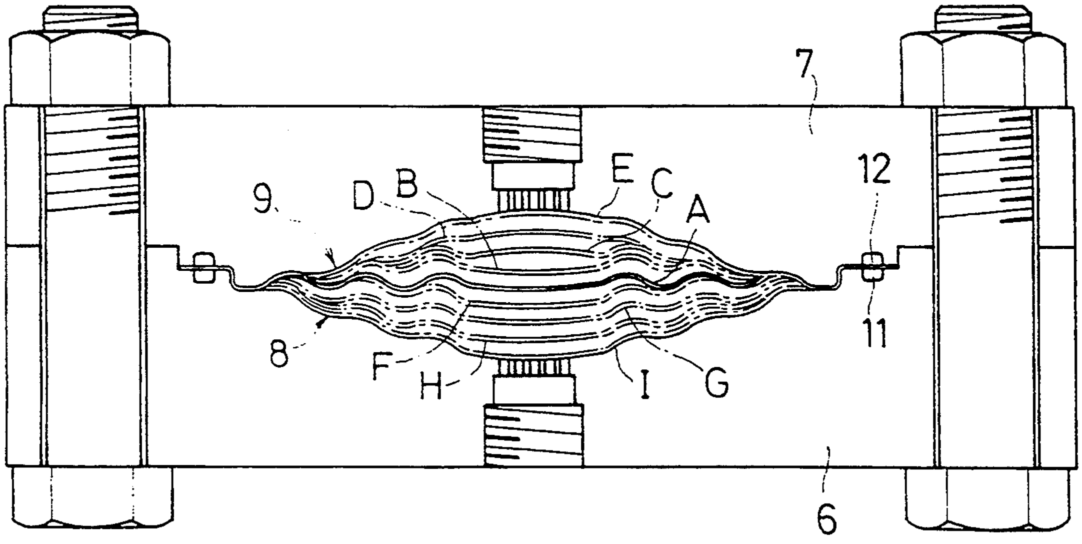
FIG. 2 shows results of an experiment carried out on the undulated diaphragm container according to the first embodiment of the present invention.

FIG. 2 shows results of an experiment in which the position of the diaphragm 1 was measured with the pressure in the fluid chamber 14 varied. In FIG. 2, the position A is an intermediate position similar to that shown by the solid lines in FIG. 1. As the pressure in the fluid chamber 14 is raised, the diaphragm 1 moves toward the gas chamber 13, that is, from the position A to the positions B, C and D successively in the mentioned order, and finally reaches the position E where the diaphragm 1 comes in contact with the recess 9 completely. As the pressure in the fluid chamber 14 is lowered, the diaphragm 1 moves toward the fluid chamber 14, that is, from the position A to the positions F, G and H successively in the mentioned order, and finally reaches the position I where the diaphragm 1 comes in contact with the recess 8 completely. Deformation of the diaphragm 1 during movement is restricted by virtue of the elasticity and rigidity of the diaphragm 1 and the structure thereof, which includes a series of alternate, approximately concentric convex and concave portions. Thus, the diaphragm 1 regularly extends and contracts, as shown in FIG. 2, without causing local inversion of the bending direction.

Figure 3:
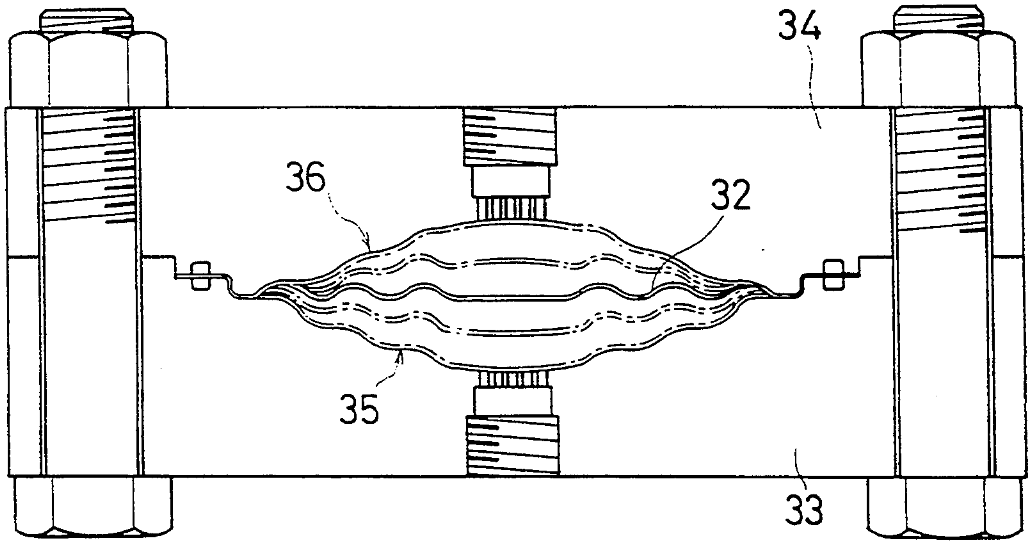
FIG. 3 is a sectional view of an undulated diaphragm container according to a second embodiment of the present invention.
Figure 4:
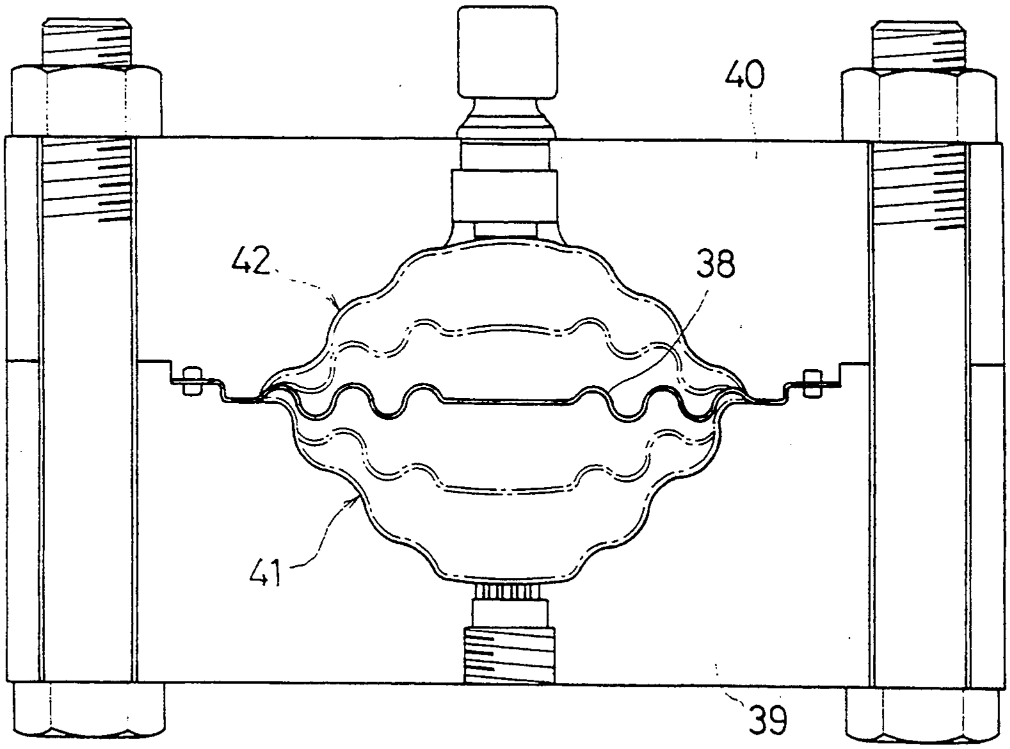
FIG. 4 is a sectional view of an undulated diaphragm container according to a third embodiment of the present invention.
Figure 5:
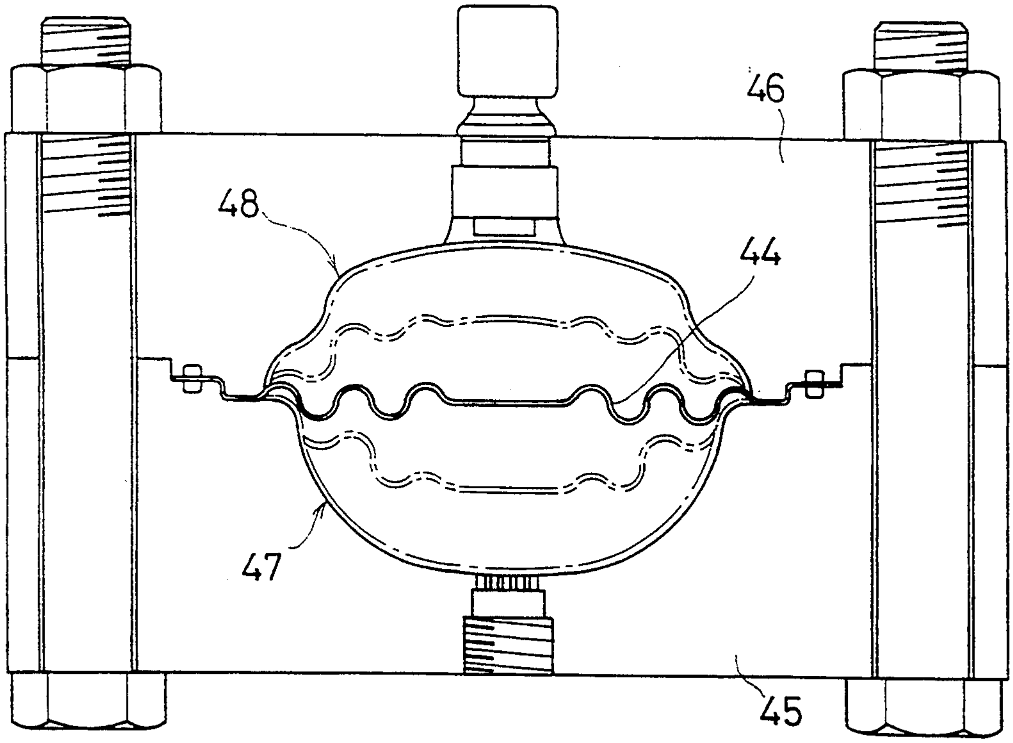
FIG. 5 is a sectional view of an undulated diaphragm container according to a fourth embodiment of the present invention.

FIG. 3 shows an undulated diaphragm container according to a second embodiment of the present invention, and FIGS. 4 and 5 respectively show third and fourth embodiments of the present invention. In the second embodiment, shown in FIG. 3, the body 33 and the side plate 34 have recesses 35 and 36, respectively, which are shallower than those in the first embodiment, and hence the gas and fluid chambers have relatively small volumes. Accordingly, the distance of travel of the diaphragm 32 is relatively short. Therefore, the diaphragm 32 in the second embodiment has two convex portions and a half and also two concave portions and a half, whereas the number of convex and concave portions of the diaphragm 1 in the first embodiment is three and a half each. The height of the approximately concentric convex and concave portions is also relatively low. Accordingly, bending and stretching stresses acting on the diaphragm 32 during movement are relatively gentle. The recesses 35 and 36 of the body 33 and the side plate 34 in the second embodiment each have a configuration corresponding to that of the diaphragm 32.

In the undulated diaphragm container according to the third embodiment, shown in FIG. 4, the body 39 and the side plate 40 have recesses 41 and 42, respectively, which are deeper than those in the first embodiment, and hence the gas and fluid chambers have relatively large volumes. Accordingly, the distance of travel of the diaphragm 38 is relatively long. Therefore, in the third embodiment the height of the approximately concentric convex and concave portions is higher than in the case of the diaphragm 1 in the first embodiment. Accordingly, bending stress acting on the diaphragm 38 during movement is relatively intense. The recesses 41 and 42 of the body 39 and the side plate 40 in the third embodiment each have a configuration corresponding to that of the diaphragm 38.

In the undulated diaphragm container according to the fourth embodiment, shown in FIG. 5, the diaphragm 44 is formed from a material having a wider allowable range for bending and stretch (i.e., lower rigidity) than in the case of the third embodiment. Since the material of the diaphragm 44 has a relatively wide allowable range for bending and stretch, the diaphragm 44 is relatively easy to bend. The recesses 47 and 48 of the body 45 and the side plate 46 each have a configuration in which the number of concave and convex portions is smaller than that in the third embodiment.

Figure 6:
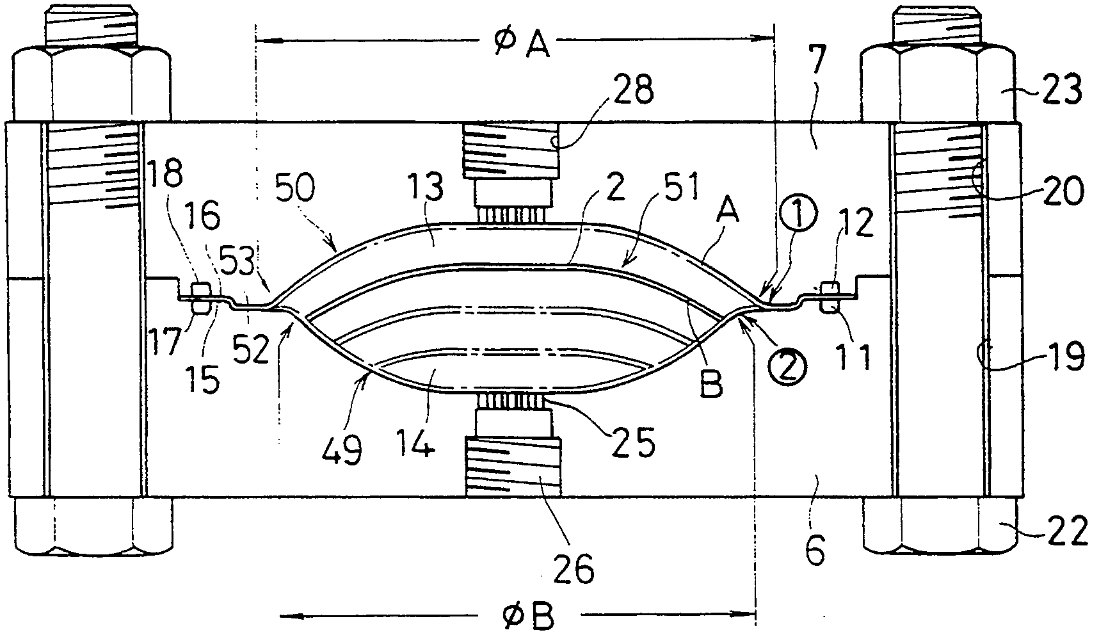
FIG. 6 is a sectional view of a diaphragm device according to a fifth embodiment of the present invention.
Figure 14:
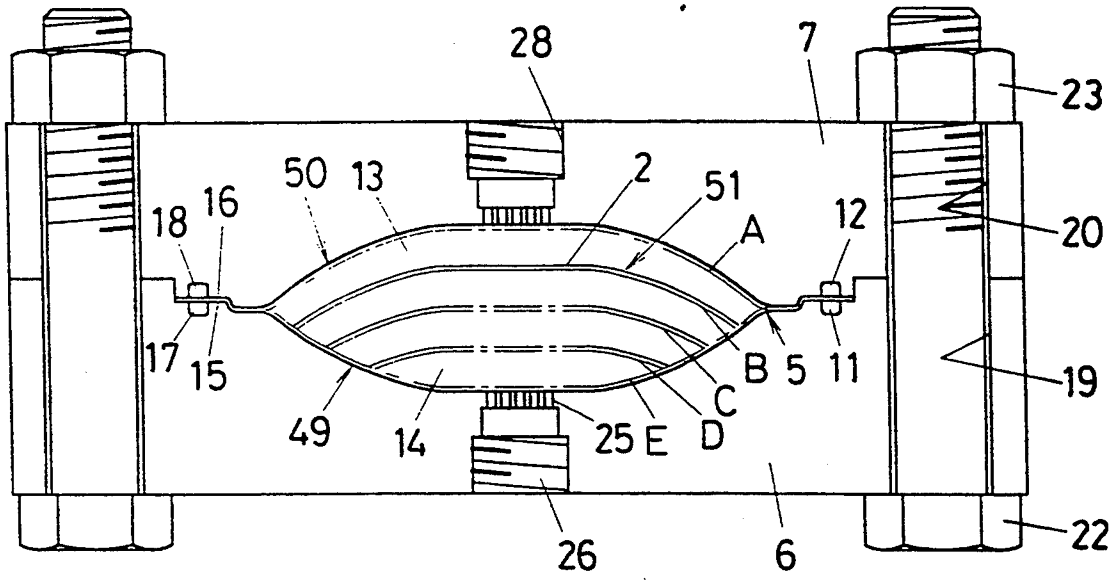
FIG. 14 is a sectional view of a conventional diaphragm device.

A diaphragm device according to a fifth embodiment of the present invention will be described below with reference to FIG. 6. In the figure, portions and members of the diaphragm device which are common to the fifth embodiment and the conventional device shown in FIG. 14 are denoted by the same reference numerals as those in FIG. 14, and description thereof is omitted. An annular flat portion 52 is formed on the inner peripheral side of the clamp portion 15 of the body 6. Similarly, an annular flat portion 53 is formed on the inner peripheral side of the clamp portion 16 of the side plate 7. A recess 49 is formed on the inner peripheral side of the inner peripheral edge ② of the flat portion 52. The boundary portion between the flat portion 52 and the recess 49 forms a gently curved surface. The diameter of the central portion of the curved surface is oB. Similarly, a recess 50 is formed on the inner peripheral side of the inner peripheral edge ① of the flat portion 53, and the boundary portion between the flat portion 53 and the recess 50 forms a gently curved surface. The diameter of the central portion of the curved surface is oA. The diameters oA and oB are different from each other by a predetermined length. When the pan-shaped diaphragm 51 moves from the position B to the position A in response to a change of the pressure in the fluid chamber 14, it begins to bend toward the recess 50 at a position in the vicinity of the circumference of the diameter oA. Similarly, when moving from the position A to the position B, the pan-shaped diaphragm 51 begins to bend toward the recess 49 at a position in the vicinity of the circumference of the diameter oB. Thus, the position where the pan-shaped diaphragm 51 bends toward the recess 50 in the vicinity of the inner periphery of the flat portion 53, that is, at the peripheral edge of the gas chamber 13, and the position where the pan-shaped diaphragm 51 bends toward the recess 49 in the vicinity of the inner periphery of the flat portion 52, that is, the peripheral edge of the fluid chamber 14, are different from each other. Accordingly, where inversion of the bending direction of the pan-shaped diaphragm 51 takes place does not concentrate on a particular portion of the diaphragm 51 at the peripheral edges of the gas and fluid chambers 13 and 14.

Figure 7:
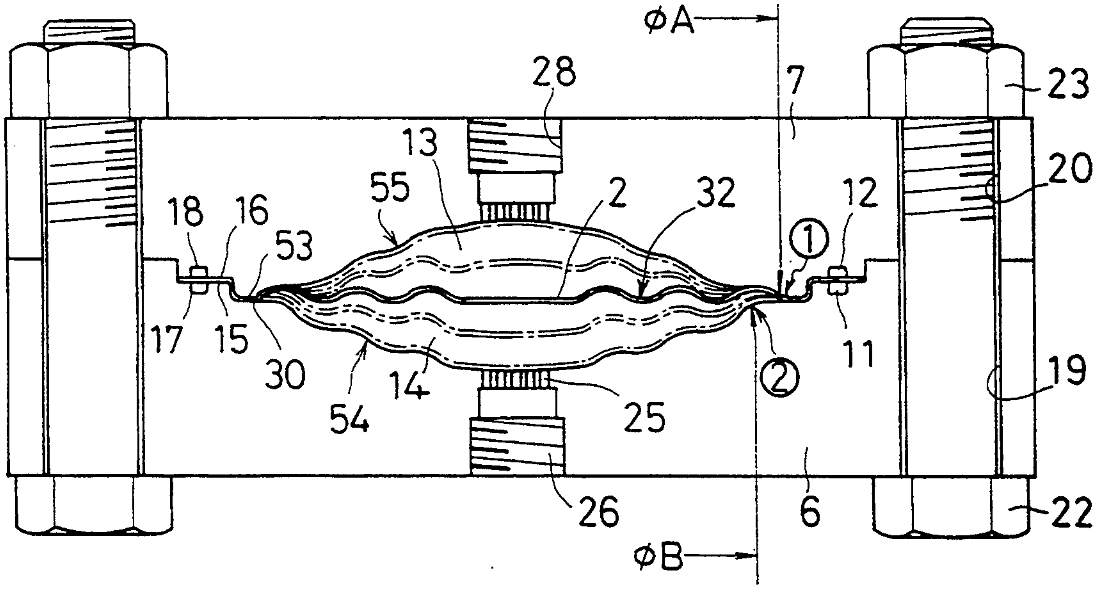
FIG. 7 is a sectional view of a diaphragm device according to a sixth embodiment of the present invention.

A diaphragm device according to a sixth embodiment of the present invention will be described below with reference to FIG. 7. The sixth embodiment is equivalent to an arrangement in which the technical idea of the first embodiment is applied to the fifth embodiment. In FIG. 7, portions and members of the diaphragm device which are common to the fifth and sixth embodiments are denoted by the same reference numerals as those in FIG. 6, and description thereof is omitted. In the sixth embodiment, an undulated diaphragm 32 which is similar to the diaphragm 1 in the first embodiment is used. That is, the undulated diaphragm 32 has an approximately circular, flat plate-shaped central portion 2, and a series of alternate, approximately concentric convex and concave portions, which are formed at the outer periphery of the central portion 2. The surfaces of recesses 54 and 55, which are provided in the body 6 and the side plate 7, respectively, are complementally formed to correspond to the convex and concave portions of the diaphragm 32 when extended, in the same way as in the first embodiment. When the undulated diaphragm 32 moves in response to a change of the pressure in the fluid chamber 14, deformation of the diaphragm 32 is restricted by virtue of the elasticity and rigidity of the diaphragm 32 and the structure thereof, which includes a series of alternate, approximately concentric convex and concave portions. Thus, the diaphragm 32 regularly extends and contracts without causing local inversion of the bending direction. In addition, there is a difference between the diameter oA of an annular portion ① where the undulated diaphragm 32 bends toward the recess 55 in the vicinity of the inner peripheries of the flat portions 52 and 53 and the diameter oB of an annular portion ② where the undulated diaphragm 32 bends toward the recess 54 in the vicinity of the inner peripheries of the flat portions 52 and 53, and therefore where inversion of the bending direction of the undulated diaphragm 32 takes place does not concentrate on a particular portion of the diaphragm 32 in the vicinity of the inner peripheries of the flat portions 52 and 53 in the same way as in the fifth embodiment.

Figure 8:
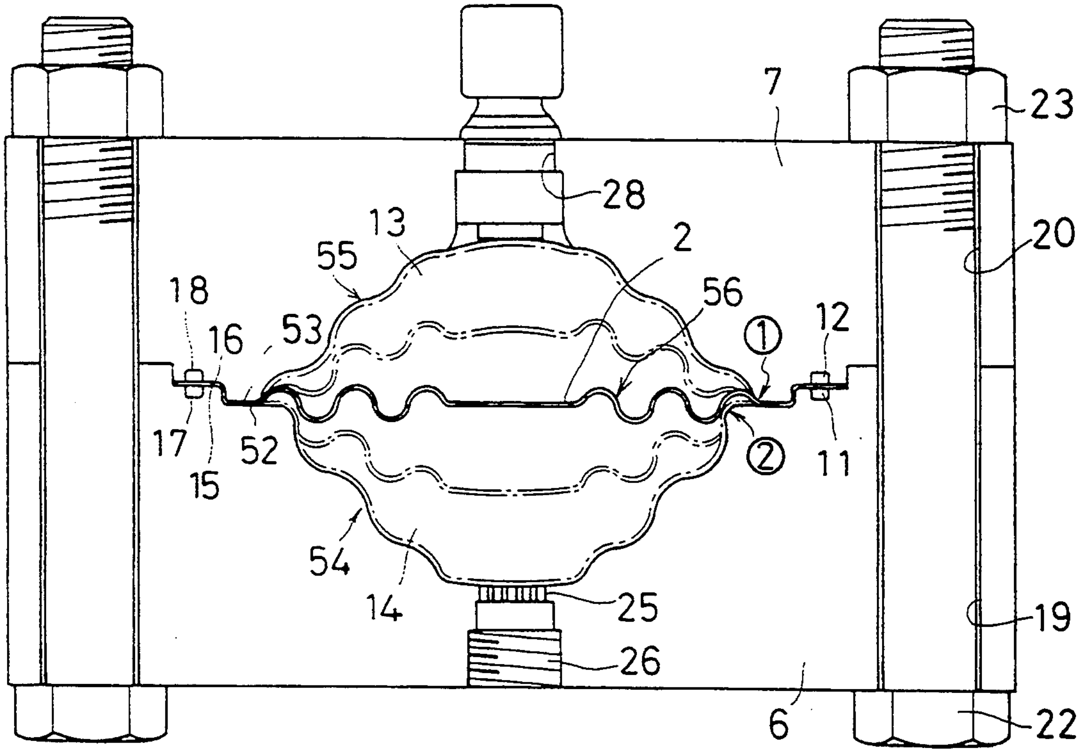
FIG. 8 is a sectional view of a diaphragm device according to a seventh embodiment of the present invention.

A diaphragm device according to a seventh embodiment of the present invention will be described below with reference to FIG. 8. In the figure, portions and members of the diaphragm device which are common to the seventh embodiment and the sixth embodiment, shown in FIG. 7, are denoted by the same reference numerals as those in FIG. 7, and description thereof is omitted. In the seventh embodiment, the body 6 and the side plate 7 respectively have recesses 54 and 55, respectively, which are deeper than those in the sixth embodiment, and the gas and fluid chambers 13 and 14 have larger volumes than those in the sixth embodiment.

Figure 9:
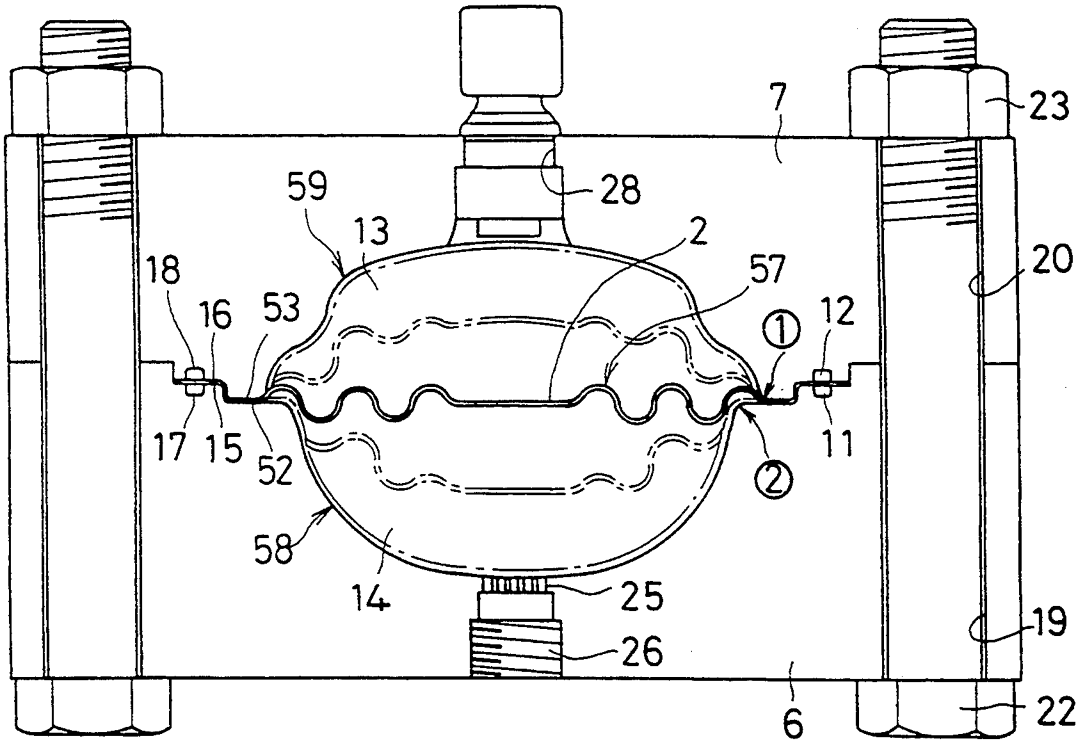
FIG. 9 is a sectional view of a diaphragm device according to an eighth embodiment of the present invention.

A diaphragm device according to an eighth embodiment of the present invention will be described below with reference to FIG. 9. In the figure, portions and members of the diaphragm device which are common to the eighth embodiment and the seventh embodiment, shown in FIG. 8, are denoted by the same reference numerals as those in FIG. 8, and description thereof is omitted. In the eighth embodiment, the undulated diaphragm 57 is formed from a material having a wider allowable range for bending and stretch than in the case of the seventh embodiment. Since the material of the undulated diaphragm 57 has a relatively wide allowable range for bending and stretch, the diaphragm 57 is relatively easy to bend. The recesses 58 and 59 of the body 6 and the side plate 7 each have a configuration in which the number of concave and convex portions is smaller than that in the eighth embodiment.

Figure 10:
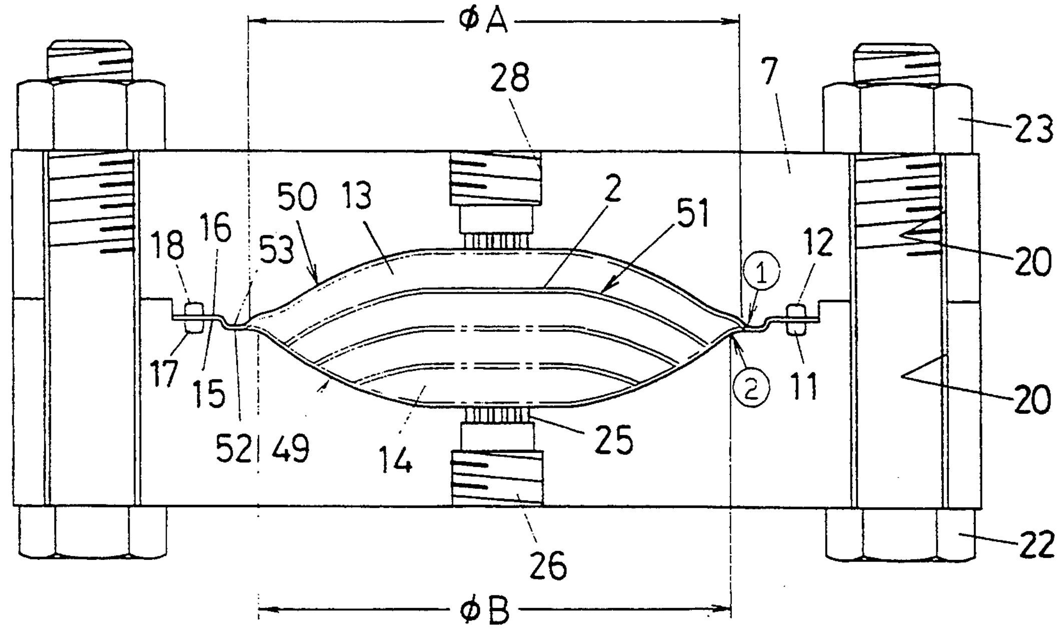
FIG. 10 is a sectional view of a diaphragm device according to a ninth embodiment of the present invention.

A diaphragm device according to a ninth embodiment of the present invention will be described below with reference to FIG. 10. In the figure, portions and members of the diaphragm device which are common to the ninth embodiment and the fifth embodiment, shown in FIG. 6, are denoted by the same reference numerals as those in FIG. 6, and description thereof is omitted.

Figure 11:
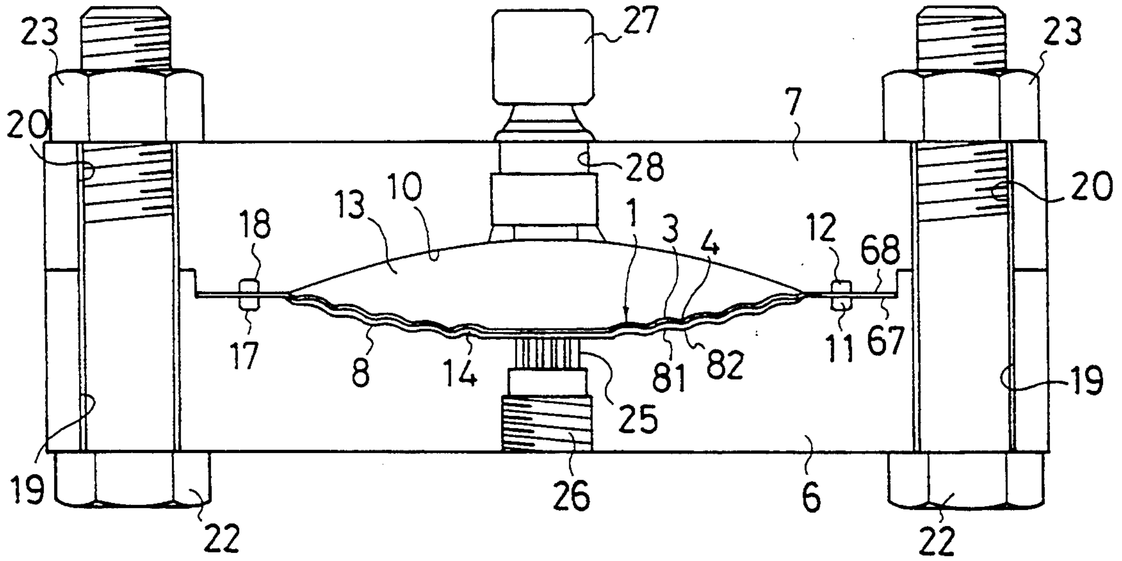
FIG. 11 is a sectional view of an undulated diaphragm container according to a tenth embodiment of the present invention.

An undulated diaphragm container according to a tenth embodiment of the present invention will be described below with reference to FIG. 1. The diaphragm 1 in the tenth embodiment is the same as that employed in the first embodiment, and hence the contents of the diaphragm 1 are as stated above in connection with the first embodiment. In FIG. 11, the same portions or members as those in FIG. 1 are denoted by the same reference numerals as those used in FIG. 1, and description of the structures of such portions or members is omitted. As shown in FIG. 11, the undulated diaphragm container according to the tenth embodiment of the present invention includes a body 6 and a side plate 7. The mutually opposing surfaces of the body 6 and the side plate 7 are respectively provided with recesses 8 (on the body 6) and 10 (on the side plate 7). In the tenth embodiment, it is premised that the undulated diaphragm 1 comes in contact with the recess 8, but there is no possibility of the diaphragm 1 coming in contact with the recess 10. On this premise, the recess 8 of the body 6 has a wall surface configuration which matches a deformed shape of the diaphragm 1 when pressed to contact the wall surface of the recess 8 by the fluid pressure, in the same way as in the first embodiment, whereas the wall surface of the recess 10 of the side plate 7 is a smooth curved surface and not shaped so as to match the shape of the diaphragm 1 which would be deformed if it is pressed against the wall surface of the recess 10, in the same way as in the fifth embodiment. In response to a change of the pressure in the fluid chamber 14, the diaphragm 1 only slightly moves toward the gas chamber 13, but it moves toward the fluid chamber 14 to a considerable extent. With the stretch movement, the diaphragm 1 can come in contact with the recess 8 but will not contact the recess 10. The diaphragm 1 has a series of approximately concentric convex and concave portions 3 and 4 which are formed so that when the diaphragm 1 extends toward the fluid chamber 14 to come in contact with the surface of the recess 8 completely, the convex and concave portions 3 and 4 of the diaphragm come in contact with concave and convex portions 81 and 82, respectively, which are formed on the recess 8, and snugly fit thereto.

Figure 12:
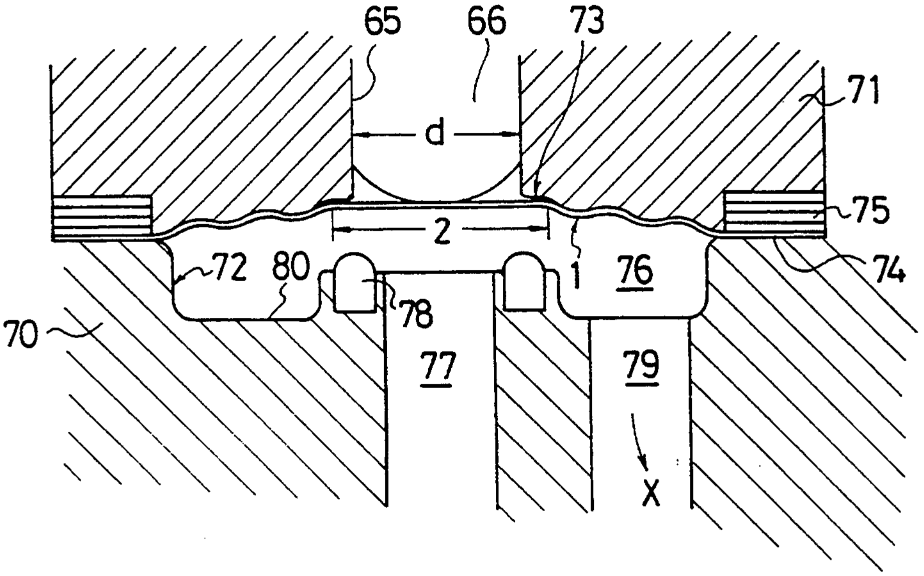
FIG. 12 is a sectional view of a metallic diaphragm device according to an eleventh embodiment of the present invention.

A metallic diaphragm device according to an eleventh embodiment of the present invention will be described below with reference to FIG. 12. The diaphragm 1 in the eleventh embodiment is made of a metallic material but has the same configuration as that of the diaphragm 1 employed in the first embodiment. As shown in FIG. 12, the metallic diaphragm device according to the eleventh embodiment of the present invention includes a valve casing 70 and a valve cover 71. The mutually opposing surfaces of the valve casing 70 and the valve cover 71 are respectively provided with recesses 72 (on the valve casing 70) and 73 (on the valve cover 71). The metallic undulated diaphragm 1 is disposed between the recesses 72 and 73. The wall surface of the recess 73 has a configuration which matches a deformed shape (wave pattern shape approximately the same as that of the diaphragm 1) of the metallic undulated diaphragm 1 when pressed to contact the wall surface of the recess 73 by the elastic force of the diaphragm 1. A cylinder bore 65 is provided to open in the center of the recess 73, and a piston 66 having the function of a valve rod is slidably fitted in the cylinder bore 65. On the other hand, the recess 72 has an inlet passage 77 which opens in the center thereof, and an annular valve seat 78 is provided at the outer periphery of the opening of the inlet passage 77. An annular hollow 80 is formed at the outer periphery of the valve seat 78, and an outlet passage 79 opens into the hollow 80. Thus, the wall surface configuration of the recess 72 does not match a deformed shape of the undulated diaphragm 1 when pressed to contact the wall surface of the recess 72. The outer peripheral portion of the diaphragm 1 is clamped between a clamp portion 74 and a diaphragm holder 75. Thus, a first chamber 76 on the recess (72) side and a second chamber on the recess (73) side are defined by the diaphragm 1. It should be noted that the diameters d of the valve seat 78 and the piston 66 are set so as to be smaller than the diameter of the central circular portion 2 of the diaphragm 1.

FIG. 12 shows the undulated diaphragm 1 which is in a state where the undulations of the diaphragm 1 are pressed against the undulated recess 73 (to be precise, the recess 73 has a configuration matching the deformed shape of the diaphragm 1 when pressed against the wall surface thereof) of the valve cover 71 by the elastic force of the metallic diaphragm 1. At this time, the diaphragm 1 lies in a totally open position where it is remotest from the valve seat 78. Therefore, the fluid passes at the highest flow rate from the inlet passage 77 toward the outlet passage 79 through the gap between the valve seat 78 and the diaphragm 1 and through the first chamber 76 as shown by the arrow X. When the piston 66 is moved toward the valve seat 78, the distal end portion of the piston 66 presses the central circular portion 2 of the diaphragm 1 toward the valve seat 78, causing the diaphragm 1 to approach the valve seat 78. As a result, the gap between the valve seat 78 and the diaphragm 1 decreases, resulting in a reduction in the flow rate of fluid passing through the first chamber 76. When the piston 66 is further moved toward the valve seat 78, the valve seat side of the central circular portion 2 of the diaphragm 1 is pressed against the valve seat 78. As a result, the flow rate of fluid passing through the first chamber 76 becomes zero. When the piston 66 is moved toward the valve cover 71 (upward as viewed in FIG. 12), the diaphragm 1 is caused to leave the valve seat 78 and move toward the valve cover 71 by its own elastic force and the force of fluid acting on the first chamber side of the diaphragm 1. As the diaphragm 1 moves away from the valve seat 78, the flow rate of fluid passing through the first chamber 76 increases. By the movement thereof, the diaphragm 1 finally comes in contact with the recess 73. A portion of the wall surface of the recess 73 which is contacted by the diaphragm 1 is composed of a series of alternate concave and convex portions, which are complementally formed to correspond to the approximately concentric convex and concave portions of the diaphragm 1 when extended. That is, when the diaphragm 1 is extended toward the valve cover 71 to come in contact with the surface of the recess 73 completely, the convex and concave portions of the diaphragm 1 come in contact with the concave and convex portions, respectively, which are formed on the recess 73, and snugly fit thereto.

Figure 13:
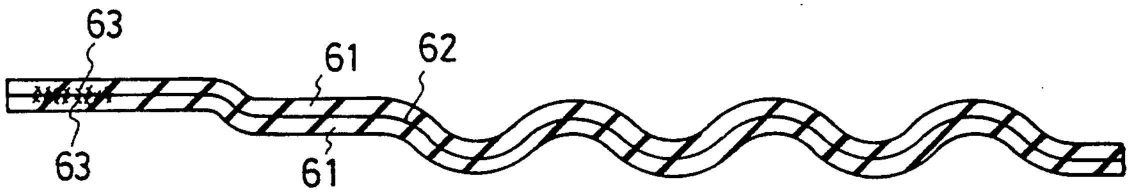
FIG. 13 is a fragmentary sectional view of one example of a diaphragm which may be used in the first to fourth and sixth to tenth embodiments of the present invention.

FIG. 13 is a fragmentary enlarged view of a diaphragm which may be used in the first to fourth, sixth to eighth and tenth embodiments of the present invention. However, a diaphragm having a gas barrier layer such as that shown in FIG. 13 may also be applied to the fifth and ninth embodiments. The illustrated diaphragm has an elastic material layer 61, which is made of an elastic material, e.g., a rubber, and a gas barrier layer 62 disposed inside the elastic material layer 61 or on one side thereof. The gas barrier layer 62 is formed by bonding a gas blocking film comprised of either a resin film of low gas permeability made of polyvinyl alcohol, polyvinyl fluoride, vinylidene chloride, etc., or a metallic foil, to at least one side of a reinforcing material, e.g., a woven or unwoven fabric. However, the gas barrier layer 62 may be formed from at least one layer of gas blocking film without using a reinforcing material. The diameter of the gas barrier layer 62 is smaller than the diameter of the elastic material layer 61. Thus, a portion of the diaphragm which lies at the outer periphery of the gas barrier layer 62 is composed only of the elastic material layer 61. The gas barrier layer 62 is bonded to the elastic material layer 61 at bonding portions 63 provided on both sides of the peripheral edge thereof, and it is also bonded to the elastic material layer 61 at the fluid chamber side thereof over the whole surface. When the diaphragm shown in FIG. 13 is applied to a diaphragm device or the like, a gas that enters the gas chamber-side elastic material layer 61 from the gas chamber may reach the gas barrier layer 62 and then move as far as the peripheral edge of the gas barrier layer 62 along the surface thereof. However, even if the gas has reached the peripheral edge of the gas barrier layer 62, the movement of the gas along the surface is blocked by the bonding portion 63. For the gas reaching the bonding portion 63 to leak, it must pass through the area between the molecules in the gas chamber-side elastic material layer 61 and in the elastic material layer 61 lying at the outer periphery of the gas barrier layer 62. The amount of gas passing through the elastic material layer 63 in this way is extremely small.

I claim:

1. A diaphragm device comprising first and second container members joined to each other along annular mating clamping surfaces, each of the first and second containers having a generally bowl-shaped recess radially inwardly of the respective clamping surface, and a disc-shaped diaphragm having a peripheral portion clamped between the clamping surfaces of the container members, a substantially flat center portion and a plurality of alternate concentric annular convex and concave portions between the peripheral portion and the center portion, and the recess of the first container member having a surface facing the diaphragm and having a plurality of alternate concentric annular convex and concave portions shaped and located so as to match the convex and concave portions of the diaphragm when the diaphragm is extended in the direction of said surface of the first container member.

2. A diaphragm device according to claim 1 wherein the recess of the second container member has a surface facing the diaphragm and having a plurality of alternate concentric annular convex and concave portions shaped and located so as to match the convex and concave portions of the diaphragm when the diaphragm is extended in the direction of said surface of the second container member.

3. A diaphragm device according to claim 1 wherein the diaphragm defines with the recess of the first container member a first chamber, the diaphragm defines with the recess of the second container member a second chamber, and the first and second chambers have different outer diameters such that a first annular bending portion of the diaphragm where the diaphragm bends when it extends toward the recess in the first container member is spaced apart radially from a second annular bending portion of the diaphragm where the diaphragm bends when it extends toward the recess in the second container.

4. A diaphragm device according to claim 3 wherein each of the first and second container members has an annular peripheral flat surface immediately radially inwardly of the clamping portion and an annular smoothly and gently curved convex surface joining the flat portion to the recess.

5. A diaphragm device comprising first and second container members joined to each other along annular mating clamping surfaces and having generally bowl-shaped recesses radially inwardly of the clamping surfaces, and a disc-shaped diaphragm clamped adjacent a peripheral portion between the clamping surfaces of the container members, the diaphragm having a substantially flat center portion and a plurality of alternate concentric annular convex and concave portions between the peripheral portion and the center portion, the diaphragm defining with the recess of the first container member a first chamber, the diaphragm defining with the recess of the second container member a second chamber, and the first and second chambers having different outer diameters such that a first annular bending portion of the diaphragm where the diaphragm bends when it extends toward the recess in the first container member is spaced apart radially from a second annular bending portion of the diaphragm where the diaphragm bends when it extends toward the recess in the second container.

6. A diaphragm device according to claim 5 wherein each of the first and second container members has an annular peripheral flat surface immediately radially inwardly of the clamping portion and an annular smoothly and gently curved convex surface joining the flat portion to the recess.

7. A diaphragm device according to claim 6 wherein the recess of the first container member has a surface facing the diaphragm and having a plurality of alternate concentric annular convex and concave portions shaped and located so as to match the convex and concave portions of the diaphragm when the diaphragm is extended in the direction of said surface of the first container member.

8. A diaphragm device according to claim 7 wherein the recess of the second container member has a surface facing the diaphragm and having a plurality of alternate concentric annular convex and concave portions shaped and located so as to match the convex and concave portions of the diaphragm when the diaphragm is extended in the direction of said surface of the second container member.

9. A diaphragm device according to claim 5 wherein the recess of the first container member has a surface facing the diaphragm and having a plurality of alternate concentric annular convex and concave portions shaped and located so as to match the convex and concave portions of the diaphragm when the diaphragm is extended in the direction of said surface of the first container member.

10. A diaphragm device according to claim 9 wherein the recess of the second container member has a surface facing the diaphragm and having a plurality of alternate concentric annular convex and concave portions shaped and located so as to match the convex and concave portions of the diaphragm when the diaphragm is extended in the direction of said surface of the second container member.

* * * * *